United States Patent [19]

Fastner

[11] 3,940,976

[45] Mar. 2, 1976

[54] METHOD OF DETERMINING THE SUITABILITY OF CONTINUOUSLY CAST SLABS OF AL- OR AL-SI-KILLED SOFT STEEL FOR PRODUCING COLD ROLLED SHEETS TO BE TINNED

[75] Inventor: Thorwald Fastner, Linz, Austria

[73] Assignee: Vereinigte Osterreichische Eisen- und Stahlwerk-Alpine Montan Aktiengesellschaft, Linz, Austria

[22] Filed: Mar. 14, 1975

[21] Appl. No.: 558,327

[30] Foreign Application Priority Data

Mar. 18, 1974 Austria .............................. 2194/74

[52] U.S. Cl. .................. 73/104; 73/432 R; 148/128
[51] Int. Cl.² .......................................... G01N 19/08
[58] Field of Search ................ 73/432 R, 105, 104; 148/128

[56] References Cited
UNITED STATES PATENTS 3,583,216   6/1971   Milewski .............................. 73/105

*Primary Examiner*—Donald O. Woodiel
*Attorney, Agent, or Firm*—Brumbaugh, Graves, Donohue & Raymond

[57] ABSTRACT

A method of determining the suitability of continuously cast slabs of Al- or Al-Si-killed soft steel for producing cold rolled sheets to be tinned, wherein from the cast strand a transverse sample of a length of 50 to 150 mm, preferably 100 mm, is taken by making parallel cuts perpendicular to the thickness of the strand, and a slanting cut is made from the one end of the sample starting from the surface thereof, which at the other end of the sample is 30 mm deep, whereupon a Baumann print is made of this cut area, which shows inclusion clouds as brown spots; upon this the whole area of the inclusion clouds is planimetered and the planimetered area in mm² is put in relationship to the slanting cut area in dm²; a use of such steels having a characteristic value thus determined of maximally 5 mm²/dm².

3 Claims, No Drawings

METHOD OF DETERMINING THE SUITABILITY OF CONTINUOUSLY CAST SLABS OF AL- OR AL-SI-KILLED SOFT STEEL FOR PRODUCING COLD ROLLED SHEETS TO BE TINNED

In slabs produced by the continuous casting process of Al- or Al-Si-killed soft steel, which have a width of 600 to 2500 mm, the molten steel is cast from a casting ladle into a tundish and from there into the continuous casting mould via immersion tubes. The level of the molten metal in the mould is covered with casting slag or casting powder. The strand is extracted from the mould while the sump is still liquid and in the secondary cooling zone it is cooled until it has solidified throughout.

There are extremely high demands on cold rolled sheets, especially tin plates intended for tinning, as regards the surface quality of the slabs; this is so because each surface fault, after tinning, is not lessened, but appears even more clearly. In soft Al- or Al-Si-killed steels line-like surface patterns occur which are caused by cloud-like accumulations of microscopic Al-oxide- or -Al-Si-oxide inclusions. Sheets having such surface patterns cannot be used for tinning, but have to be used for lesser purposes.

It is very difficult to produce tin sheets that are free from the above mentioned surface faults, since the thickness of the sheets, which amounts to about 0.2 mm, is very low. During the rolling process the inclusion-clouds come to the surface of the rolling stock, depending on the thickness of the cast-or sheet product, because the inclusions are not deformed during rolling. The thinner the sheet becomes, the larger the inclusions become relative to the sheet thickness. Finally, the inclusions cut through the surface and become apparent. In tin sheets the surface quality is impaired by inclusion-clouds which lie in the slabs up to 30 mm deep.

The invention has as its object to find a characteristic value for the oxidic inclusions which allows for a simple determination of the suitability of cast steel slabs for the production of sheets to be tinned.

The method of the invention by which this object is achieved consists in that, from the cast strand, a transverse sample of a length of 50 to 150 mm, preferably 100 mm, is taken by making parallel cuts, perpendicular to the thickness of the strand, and that from one end of the sample, a slanting cut, starting from the surface thereof, is made which at the other end of the sample is 30 mm deep, whereupon a Baumann print is made of this cut area which shows inclusion clouds present as brown spots, and then the whole area of the inclusion clouds is planimetered and the planimetered area in mm$^2$ is put in relation to the slanting cut area in dm$^2$.

Slanting cuts on the surface have proved especially useful for determining the degree of purity. In this way a large region of the critical rim zone is covered. Samples of a length of 100 mm — viewed in the direction of casting — are considered to be the best ones. Samples that are shorter than 50 mm are not as telling. Samples that are longer than 150 mm are disadvantageous because of the wear of material.

If in this determination a value is obtained in which the characteristic value is not more than 5 mm$^2$/dm$^2$, then such slabs are suited for the production of tinned sheets.

Continuously cast steel slabs whose purity in the surface zone has characteristic values not exceeding 5mm$^2$/dm$^2$ can be produced by subjecting the molten steel in the tundish to a special cleaning and by controlling the casting conditions in the mould, as has been known per se. It has already been recommended in proposals partly not yet belonging to the prior art, to flush the steel when it flows through the tundish, preferably over the whole cross-section, continuously with inert gas; to furthermore upwardly deflect, at an angle of 5° to 45°, the steel in the mould by two opposite casting tube outlets directed toward the narrow side of the mould and also to control the outflow speed of the steel from the casting tube outlets so that a turbulent current is created which prevents or reduces deposits in the area of the strand skin up to a thickness of 30 mm. Such turbulent currents can be obtained for instance when the casting tube outlets are 40 to 80 cm away from the side walls of the mould with outflow speeds of 60 to 120 cm/sec. The gas flushing in the tundish can take place in a known manner, for instance by means of porous bricks arranged in the bottom of the tundish. Due to this gas flushing, most of the impurities present are brought to the surface and accommodated by a slag layer. This is a pre-cleaning. Also during a deflection in the mould slag particles still present are brought to the surface and accommodated by a layer of casting powder.

The method of the invention shall now be described in greater detail by way of an example.

Steel of the following chemical composition was cast for the production of tin sheet in a slab strand casting plant:

| C | 0.06% | P | 0.015% |
|---|---|---|---|
| Si | 0.06% | S | 0.017% |
| Mn | 0.30% | Al | 0.022% |

The mould was adjusted to a size of 1000 × 225 mm. The withdrawal speed was 0.8 m/min. In the tundish the steel was continuously flushed. Therein the use of N$_2$ as flush gas was 50 Ncm$^3$/kg steel. The immersion tube had two outlets of equal size. They were upwardly inclined by less than 20° — relative to the horizontal — and had a circle-cross-section with a diameter of 45 mm. This resulted in an outflow speed out of the casting tube openings of 95 cm/sec. The turbulence occurring at the front of solidification under the above described conditions ensures a very pure rim zone. A determination of the inclusion characteristic value according to the method of the invention gave 4 mm$^2$/dm$^2$ and thus it is within the range of the inclusion content permissible for tin sheets. No surface faults could be found on the tinned sheets.

What I claim is:

1. A method of determining the suitability of continuously cast slabs of Al- or Al-Si-killed soft steel for producing cold rolled sheets to be tinned, comprising taking a transverse sample of a length of between 50 and 150 mm by making parallel cuts perpendicular to the thickness of the strand and making a slanting cut in the sample, which cut starts from one end of the sample from the surface thereof and is 30 mm deep at the other end of the sample, thus creating a slanting cut area, subsequently making a Baumann print of the slanting cut area showing inclusion clouds present as brown spots, thereupon planimetering the whole inclusion-clouds-area and putting the planimetered area in mm$^2$ in relationship to the slanting cut area in dm$^2$.

2. A method as set forth in claim 1, wherein the transverse sample is 100 mm long.

3. Sheet to be tinned produced from a continuously cast slab of Al- or Al-Si-killed soft steel, which slab, when subjected to the method of claim 1, exhibits a relationship of planimetered area to slanting cut area of a maximum of 5 mm²/dm².

* * * * *